United States Patent [19]

Burke

[11] Patent Number: 5,431,660

[45] Date of Patent: Jul. 11, 1995

[54] SPRING LOADED SCREW AND DRIVER/EXTRACTOR THEREFOR

[76] Inventor: Dennis W. Burke, 245 Highland Ave., Milton, Mass. 02186

[21] Appl. No.: 159,806

[22] Filed: Nov. 30, 1993

[51] Int. Cl.$^6$ .............................................. A61B 17/18
[52] U.S. Cl. ........................................ 606/104; 411/1; 411/536; 81/429; 606/73
[58] Field of Search ................. 606/73, 104; 81/429; 411/132, 134, 396, 536, 1, 12, 11, 10, 368, 369, 544, 531

[56] References Cited

U.S. PATENT DOCUMENTS

| | | | |
|---|---|---|---|
| 3,183,762 | 5/1965 | Poupitch | 411/12 |
| 4,296,656 | 10/1981 | Ernst | 81/429 |
| 4,421,112 | 12/1983 | Mains et al. | |
| 4,567,885 | 2/1986 | Androphy | |
| 4,718,413 | 1/1988 | Johnson | |
| 4,759,350 | 7/1988 | Dunn et al. | |
| 4,787,383 | 11/1988 | Kenna | |
| 4,791,919 | 12/1988 | Elloy et al. | |
| 4,825,857 | 5/1989 | Kenna | |
| 4,892,093 | 1/1990 | Zarnowski et al. | |
| 4,909,012 | 3/1990 | Thomspon et al. | 411/544 X |
| 4,926,847 | 5/1990 | Luckman | |
| 5,042,983 | 8/1991 | Rayhack | |
| 5,129,909 | 7/1992 | Sutherland | |
| 5,139,499 | 8/1992 | Small et al. | 606/104 X |

FOREIGN PATENT DOCUMENTS 1061807 12/1983 U.S.S.R. .................................. 606/73

OTHER PUBLICATIONS

"Total Knee Arthroplasty Using the First Instruments and the Synatomic Total Knee System", DePuy Inc., 1985.
"MGII Total Knee System", Zimmer, Inc., 1989.
"MGII Total Knee System Surgical Technique", Zimmer Inc., 1989.
"Concepts in External Fixation", David Seligson and Malcolm Pope 1982, p. 252.

Primary Examiner—Peter A. Aschenbrenner
Attorney, Agent, or Firm—Wolf, Greenfield & Sacks

[57] ABSTRACT

A spring loaded screw and an associated driver for use in orthopedic applications, particularly for temporarily securing cutting guides and the like to the tibia and femur for preparation of the bone surfaces in a total knee replacement. A slidable sleeve on said screw is spring biased away from the driver. As the screw sleeve seats, the sleeve slides upwardly against the compression spring to disengage the driver from the proximal end of the screw. The driver contains a slidably disposed central cylinder which can be axially moved by sliding an externally mounted sleeve. To retract the screw, the driver sleeve is advanced toward the screw to urge the cylinder toward the proximal end of the screw sufficiently far to enable grasping of the proximal end of the screw for retraction thereof.

20 Claims, 6 Drawing Sheets

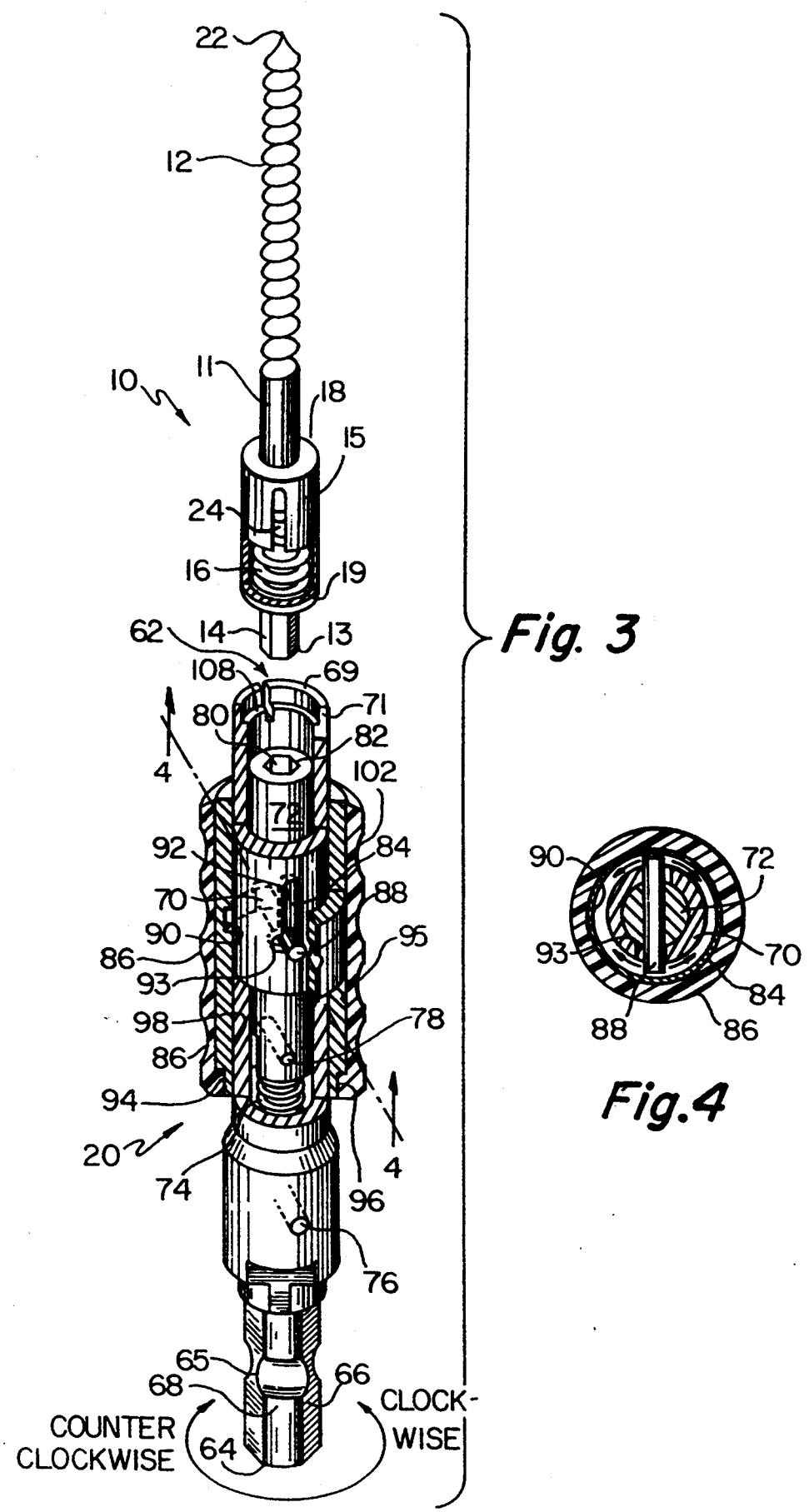

SPRING LOADED SCREW AND DRIVER/EXTRACTOR THEREFOR

FIELD OF THE INVENTION

This invention relates generally to the fixation of orthopedic prosthetics, and more particularly to a screw and complimentary driver/extractor for temporary attachment of cutting guides and other apparatus to a bone for preparation of a bone surface for attachment of a prosthesis.

BACKGROUND OF THE INVENTION

Prosthetic joint components have long been known and used in the art. Examples include knee, hip and elbow replacements. Prosthetic components are available from manufacturers such as Zimmer, Inc. of Warsaw, Ind. To prepare the bone surfaces for attachment of the prosthetic components, it is often necessary to make a series of cuts in the bone or to remove portions of the bone to cause the bone to conform to the size and shape of the components which are to be attached thereto. Every surgeon strives for precise cuts, since the more precise the cut, the more likely is the prosthetic component to be anatomically correct. An anatomically correct component provides a superior result and will last longer than one that is not anatomically correct.

One situation in which such bone cutting is required is in the preparation of the femur and tibia for a total knee replacement. Exemplary knee replacements are available from Zimmer, Inc. under the trademark MGII. In particular, implantation of press-fit, non-cemented total knee components requires very precise bone cuts. In some prosthetics, an exact fit is required for the successful bone-ingrowth fixation of joint replacement components.

Typically, bone cuts are made by an oscillating saw or a reciprocating saw utilizing cutting guides or jigs stabilized by pinning and clamping. Various guides and methods for temporarily but rigidly securing these guides to the bone surfaces have been developed. Examples are found in U.S. Pat. Nos. 4,787,383; 4,825,857; and 5,129,909. In particular, in U.S. Pat. No. 5,129,909, screws are utilized for securing the guides to the bone so that the guide is held in compression against the bone. Proper and rigid affixation of the guides to the bone are required to assure reproducibly accurate bone cuts, prosthetic seating and lower limb alignment. However, some existing guides have been found to be undesirable because there was inadequate rigid fixation of the cutting block to the bone. As a result, in some cases, it was difficult, if not impossible, to predictably achieve a precise fit of the femoral component on the distal femur.

When cutting the bone, it is important that the guides be secured immovably to the bone and that the guides be secured with the same force at each point to prevent tilting of the guide. The load applied by a screw or other fixation device should be the same predetermined value at each point of attachment. The fixation device should also be able to accommodate lateral forces applied to the guides without allowing the guides to move and without releasing the load.

If screws are used, there is a risk of the surgeon stripping the threads if too much torque is applied to the screw after it seats, thus making it difficult, if not impossible, to secure the guide rigidly to the bone in the desired location. In addition, difficulty may be achieved in removing the screw from the bone once the cutting procedure has been completed.

It is therefor an object of the present invention to provide an improved system for affixing cutting guides and the like to bone surfaces for preparation of those surfaces for the attachment of a prosthetic component.

It is another object of the present invention to provide a fixation device for cutting guides and the like for preparation of a bone surface for attachment of a prosthetic component, which fixation device can be installed with a reproducibly accurate load and can be readily extracted thereafter.

SUMMARY OF THE INVENTION

The foregoing and other objects of the invention are achieved in accordance with the present invention which includes a spring loaded screw and an associated combined driver and extractor.

The screw of the present invention includes a conventional lag screw having a spring loaded sleeve adjacent its proximal end. The sleeve is normally held by a spring in a position away from the proximal end of the screw to permit engagement of the proximal end by a suitably configured driver. As the screw penetrates into the bone, and as the lower surface of the sleeve seats, further advance of the screw into the bone causes the sleeve to ride upwardly toward the proximal end of the screw lifting the driver out of torque transmitting engagement with the proximal end of the screw. Further advance of the screw into the bone is thereby prevented and the spring applies a predetermined load on the guide.

The combined driver and extractor to be used with the spring loaded screw includes a driving cylinder having a recess which is configured to engage the proximal end of the screw for transmission of torque thereto. On the opposite, proximal end of the driver/extractor is a coupling configured to be received into the chuck of a tool or appliance for rotation of the screw. The driving cylinder is slidably disposed within a shaft. In its normal operating position, the driving cylinder is retained by a spring in a position in which the recess is withdrawn into and spaced from the distal end of the shaft. As the screw is advanced into the bone, the sleeve of the screw rests on a shoulder formed on interior surfaces of the distal end of the shaft and the proximal end of the screw is engaged by the recess in the driving cylinder. As the sleeve on the screw rises upwardly upon seating of the sleeve and further advance of the screw, the screw sleeve lifts the driver upwardly with respect to the screw and thus lifts the driving cylinder out of engagement with the proximal end of the screw. A clutch mechanism is provided to prevent axial movement of the driving cylinder during advance of the screw so that the driving cylinder is lifted off the proximal end of the screw at the proper point to prevent over-tightening of the screw and/or stripping of the threads.

When it is desired to extract the screw, an outer sleeve is manually rotated to release the driving cylinder through the clutch mechanism and the sleeve is urged downwardly toward the distal end of the shaft. Movement of the outer sleeve also urges the interior driving cylinder downwardly with respect to the shaft against the force of the driver spring so that the recess on the driving cylinder is no longer recessed with respect to the distal end of the shaft. At this point, the recess of the interior driving cylinder is again positioned to engage the proximal end of the screw for removal of the screw. As the screw is extracted, the driver spring returns the driving cylinder to its normal, retracted position, while the screw spring returns the screw sleeve to its normal position. The outer sleeve of the driver is rotatably mounted on the exterior surface of the shaft to allow the outer sleeve to be grasped by the user during initial extraction of the screw.

The combination of the driver/extractor and the spring loaded screw permits the application of a fixed, predetermined load at each point on the guide to prevent tilting of the guide. Also, the screw spring continues to apply a load, even if the screw is loosened. Finally, accurate placement of the screw within the bone is achieved and stripping of the screw threads is prevented. This combination also permits easy extraction of the screw by the same tool once the cutting process has been completed.

BRIEF DESCRIPTION OF THE DRAWINGS

The objects, advantages and features of this invention will be more clearly appreciated from the following detailed description when taken in conjunction with the accompanying drawings in which:

FIG. 3 is a partially cutaway, perspective view showing the screw and driver of the present invention;

FIG. 4 is a cross-sectional, end view taken along a line 4—4 of FIG. 3;

DETAILED DESCRIPTION OF THE PREFERRED EMBODIMENTS

Figure 1:
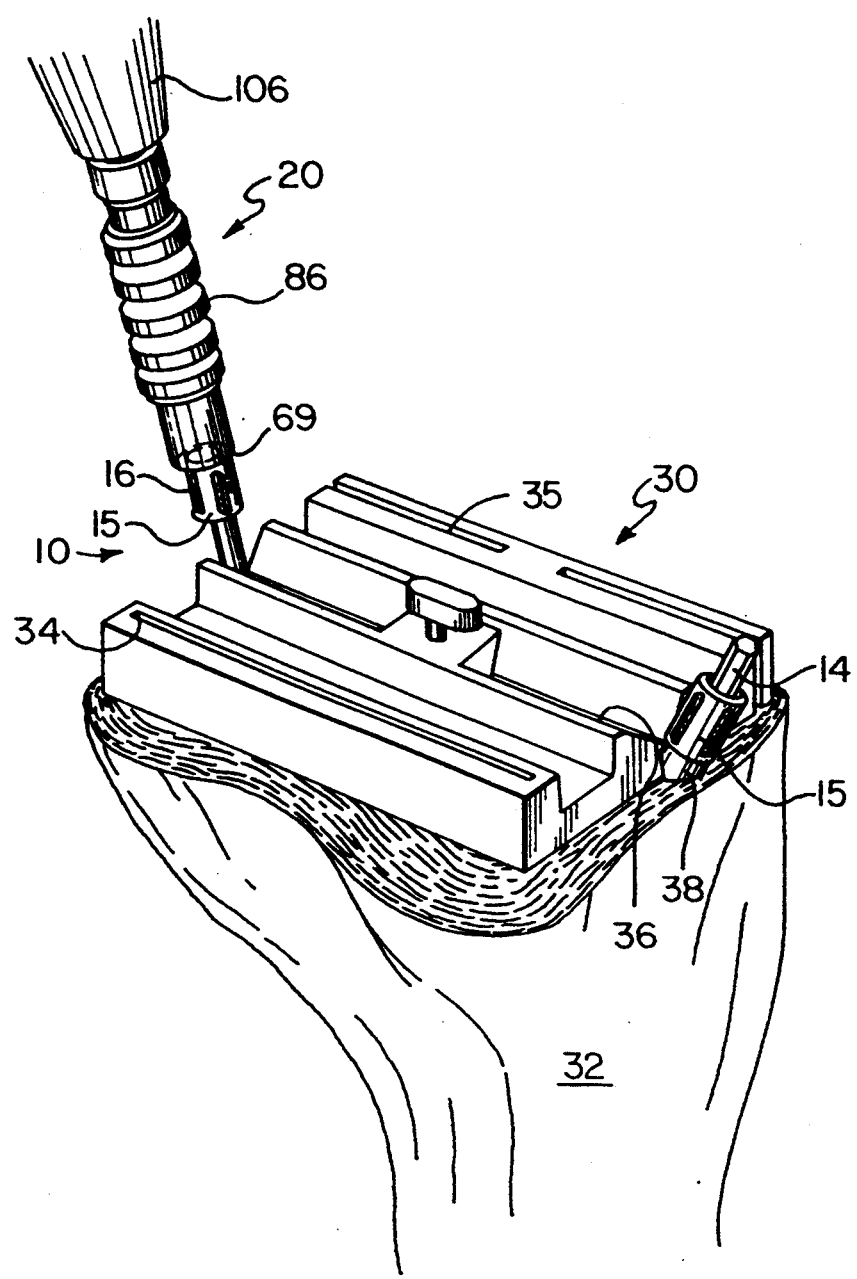
FIG. 1 is a partial, perspective view showing the screw and driver of the present invention when used in conjunction with a typical femoral finishing guide.
Figure 2:
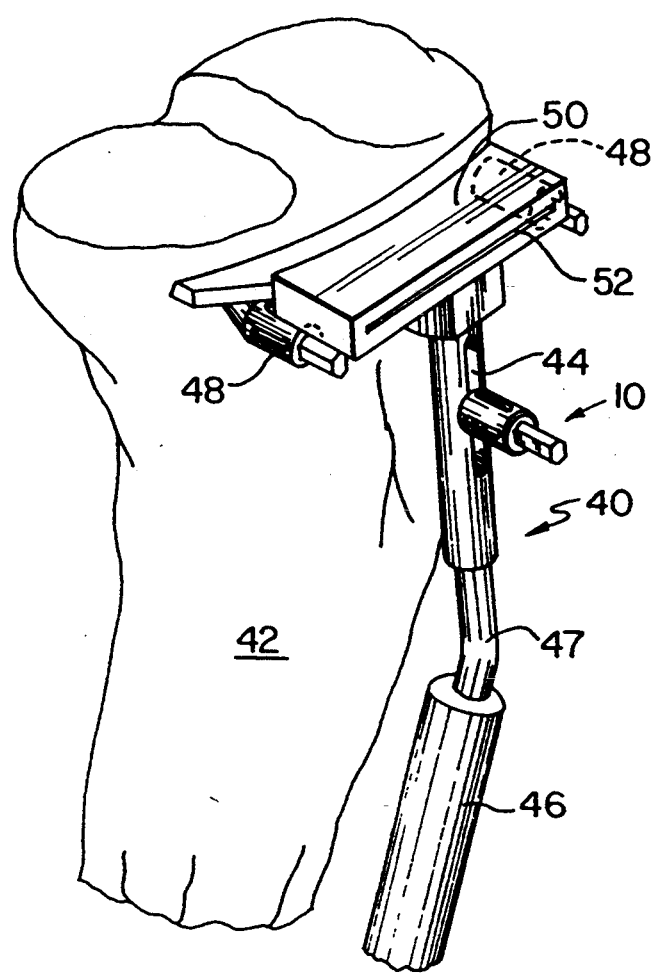
FIG. 2 is a partial, perspective view showing use of the screw of the present invention with a typical tibia cutting guide.

With reference now to the drawings, and more particularly to FIGS. 1 and 2 thereof, use of screw 10 and driver 20 of this invention will be described with particular reference to preparing a knee joint for a total knee replacement. However, it is to be understood that the screw and driver of the present invention have equal applicability to any other orthopedic procedure that requires the temporary mounting of a guide, jig or any other device used to assist in the machining or cutting of a bone surface in preparation for the mounting of a prosthetic component thereto.

Prior to installation of a total knee replacement, the distal femur and proximal tibia must be prepared to receive the respective components of the knee prosthesis. The instruments used for preparation of the distal femur include, typically, a femoral alignment guide, a femoral cutting guide an A/P measuring guide and a femoral finishing guide. The instruments used for preparing the proximal tibia typically include a tibial cutting guide and tibial depth resection guide. After opening the damaged knee area, a surgeon typically sequentially utilizes these instruments to prepare the patient's distal femur and proximal tibia ends. The precise apparatus used, and the technique employed by the surgeon are not a part of this invention and will not be described herein. Both the technique and the instruments vary from surgery to surgery and from surgeon to surgeon, and various techniques and instruments are known to those skilled in the art. Exemplary instruments and techniques are found in the following patents: U.S. Pat. Nos. 4,567,885; 4,718,413; 4,759,350; 4,791,919; 4,892,093; 5,129,909; 4,787,383; 4,825,857; and European Patent No. 0243109.

FIG. 1 illustrates the use of screw 10 in conjunction with an exemplary femoral finishing guide 30 for resecting femur 32. The attachment of finishing guide 30 is temporary as it must be removed prior to the installation of the knee replacement. Guide 30 is attached to the prepared end surface of the distal femur 32 and includes a flat undersurface that fits closely over the prepared distal femur end. Guide 30 includes anterior and posterior condyle cutting slots 34 and 35 and chamfer cutting slots 36. The posterior condyle is cut at cutting slot 35 and the anterior condyle is cut at cutting slot 34 to square the surface at a right angle to the distal femur end surface. The posterior and anterior chamfers are cut at slots 36. It is very important that guide 30 be precisely, rigidly and evenly placed on the proximal end of femur 32. It is also important that guide 30 be easily removed when the cutting operations have been completed. Therefore, it has been the practice in some existing devices to utilize screws to affix guide 30 to the proximal end of femur 32. Because the bone is somewhat softer than the screw, the surgeon must be very careful not to insert the screw too far or turn it too tightly for fear of stripping the threads and thereby making it difficult to secure guide 30 firmly in the proper position. Once the threads have been stripped, one cannot simply move the guide to a different location and reinsert the screw, since the guide would no longer be placed in the precisely required position. Moreover, once the screw has been inserted, occasionally difficulty is encountered in removing it without damaging the bone.

Utilizing this invention, two screws 10 are utilized for guide 30, one at each end of guide 30 to deter rotation of guide 30. Screws 10 are positioned such that they do not interfere with the cutting operation. Thus, screws 10 are spaced from slots 34 and 35 and are disposed beyond the ends of slots 36. Screws 10 pass through appropriately configured screw receiving members 38 which are affixed to the body of guide 30.

FIG. 2 illustrates screw 10 of this invention when used in conjunction with tibial cutting guide 40 for resecting the proximal tibia 42. Guide 40 is typically positioned between the ankle and a point on the upper tibia 42 that is close to the proximal end of tibia 42. Guide 40 should also be centered laterally between the ankle and the point on the upper tibia. A typical guide 40 includes telescoping tube 46, rod 47 and cutting platform 50. Cutting platform 50 is secured to the end of rod 47. A slot 52 is formed in platform 50 for guiding a saw blade (not shown) fitted therethrough. A saw blade is typically inserted through slot 52 to cut across the proximal tibia and to remove a bone portion to leave a flat surface suitable for accepting a prosthetic component (not shown). Platform 50 can also be used with a tibial resection guide (not shown).

Tibial cutting guide 40 is typically secured to the tibia 42 with screws 10 which are inserted through a slot 44 in rod 47 and holes 48 in cutting platform 50. Typically, slot 44 is elongated and allows for positioning of screw 10 at the desired location on the tibia 42 and adjustment of the position of platform 50. The screw in slot 44 inhibits rotation or lateral movement of tube 40, while screws in holes 48 permit precise location of platform 50. The position of tube 46 can be adjusted with respect to rod 47 to accommodate the particular length of the tibia 42 upon which the operation is to be performed. Often, it is necessary to readjust the position of platform 50, so that screws 10 must be removed from holes 48 and reinserted at a different location. It is evident that again, it is important that screws 10 be firmly implanted, but that the threads not be stripped, so that guide 40 is firmly secured to tibia 42. Also, it is evident that one must be able to readily unscrew screws 10 for removal of guide 40 once the cutting operations have been completed.

Screw 10 and driver 20 will now be described with particular reference to FIGS. 3 and 4. Screw 10 includes a sleeve 15, a spring 16, a central shaft 11 having threads 12 extending from a distal end 22 toward the center of shaft 11, and a coupling on proximal end 13 configured to be inserted into a cooperatively formed recess 80 in driver 20. Typically, proximal end 13 has a hexagonally-shaped cross-sectional configuration defined by six flat, angularly disposed surfaces 14 that extend parallel to the axis of shaft 11. However, other suitable, known configurations can be used.

Sleeve 15 is slidably mounted on shaft 11 between threads 12 and proximal end 13. Disposed within sleeve 15 and surrounding shaft 11 is compression spring 16. Spring 16 is captured between ridge 17 which extends around the outer perimeter of shaft 11 and end surfaces 18 of sleeve 15. Axial travel of sleeve 15 along shaft 11 toward distal end 22 is limited by lip 19 formed on the upper end of sleeve 15 which is urged against ridge 17 by spring 16. Axial travel of sleeve 15 toward proximal end 13 is restrained by spring 16, but is permitted to a limited extent, depending on the axial force applied to sleeve 15. End walls 18 of sleeve 15 may extend at substantially right angles to shaft 11, as shown in FIG. 3, or walls 18 may taper toward distal end 22 at a non-perpendicular angle with respect to shaft 11. A tapered configuration of walls 18 would make possible the seating of screw 10 in a chamfered hole in a guide 30 or 40. The side walls of sleeve 15 typically are provided with a plurality of axially extending slots 24, such as four, to permit easy cleaning and sterilization of screw 10.

Threads 12 typically terminate at a point at distal end 22 to facilitate the entry of screw 10 into a bone. The point at distal end 22 is formed into a trochar-like point to allow screw 10 to be self-starting in a bone surface to obviate predrilling of the hole. Screw 10 preferably is a lag screw and threads 12 may have any configuration typically used for a bone screw, to permit the advance of screw 10 into the bone.

Driver 20 will now be described with particular reference to FIGS. 3 and 4. Driver 20 includes shaft 70, driver cylinder 72, spring 74, coupling 65, sleeve 84 and sleeve cover 86. Coupling 65 is disposed on proximal end 64 and is adapted to have mounted thereon a conventional, manual or power appliance (not shown) for rotation of driver 20. Coupling 65 is configured to be inserted into the chuck (not shown) of such an appliance and, in one embodiment, as shown in FIG. 3, coupling 65 contains three angularly disposed, flat surfaces 66 interconnected by surfaces 68.

Cylindrical shaft 70 extends from coupling 65 toward distal end 62 and includes distal end walls 69 separated by axial slots 71. Shaft 70 is secured to or is integral with coupling 65. Driver cylinder 72 is disposed within shaft 70 substantially along the axis of shaft 70 and is preferably coaxial therewith. Cylinder 72 is permitted to slide in an axial direction with respect to shaft 70. Movement of cylinder 72 is restrained by extension spring 74 which is affixed at one end to a peg 78 on the proximal end of cylinder 72 and at the other end to a peg 76 within the central cavity of shaft 70 adjacent coupling 65. Spring 74 thus biases cylinder 72 in a direction toward proximal end 64. In this normal, biased condition, the distal end of cylinder 72 is recessed within end walls 69 of shaft 70. On its distal end, cylinder 72 contains a recess 80 which is configured to receive in a torque transmitting relationship proximal end 13 of screw 10. Typically, recess 80 has a hexagonal cross-sectioned shape, as does proximal end 13, and includes six axially extending lateral surfaces 82. Shoulders 108 are formed on the inner surfaces of walls 69 to receive sleeve 15 of screw 10. Axial slots may be formed in walls 69 to provide walls 69 with some degree of flexibility to accept a slightly enlarged sleeve 15.

Slidably disposed on the outside surface of shaft 70 between proximal end 64 and distal end 62 are a sleeve 84 and a sleeve cover 86. Both sleeve 84 and cover 86 are cylindrical in shape and are concentric with shaft 70. Sleeve 84 completely surrounds shaft 70 while cover 86 completely surrounds sleeve 84. Sleeve 84 and cover 86 are slidable in an axial direction with respect to shaft 70, and are rotatable with respect to shaft 70.

A pin 88 extends through a similarly configured channel in cylinder 72 at a point intermediate spring 74 and recess 80. The ends of pin 88 extend into and ride along groove 90 formed around the circumference of the interior surface of sleeve 84. Pin 88 passes through elongated slots 92 formed on opposite sides of shaft 70. As sleeve 84 rotates with respect to shaft 70, each end of pin 88 travels along groove 90.

Slots 92 are elongated in a direction parallel to the axis of shaft 70. Each slot 92 typically includes an extension 93 which extends at a substantially 90° angle with respect to the axial direction of elongation of slot 92. Extensions 93 and pin 88 and spring 74 cooperate to effectively act as a clutch mechanism. Spring 74 is provided with a slight rotational torque in a counter-clockwise direction as viewed from the bottom of FIG. 3. Spring 74 thus applies to cylinder 72 a counterclockwise rotational torque and an axial force toward proximal end 64 with respect to shaft 70. This torque and force cause the ends of pin 88 to move into and seat in extensions 93 in the normally retracted condition of cylinder 72. This seating serves to effectively lock pin 88 in an axial direction closest to proximal end 64 to prevent unwanted axial movement of cylinder 72 toward the distal end 62 of shaft 70. Extensions 93 extend in directions such that rotation of coupling 65 in a clockwise direction, as shown in FIG. 3, drives pin 88 into extensions 93, so that torque is transmitted through pin 88 from shaft 70 to cylinder 72.

Sleeve 84 is linked to sleeve cover 86 by lip 94 of cover 86 which extends into a similarly formed cutout 96 in sleeve 84. In addition, a ridge 98 formed on the inner surface of cover 86 extends into a similarly shaped groove 95 formed on the outer surface of sleeve 84. Ridge 98 and groove 95, as well as lip 94 and cutout 96 restrict any axial movement of sleeve 84 with respect to sleeve cover 86. If desired, the outer surface of cover 86 can be provided with a knurled gripping surface, or with undulations 102 configured to conform to the shape of the users fingers to allow the user to better grasp cover 86.

From the foregoing, it can be seen that should the user exert an axial pressure on cover 86 toward distal end 62, lips 94 and cutout 96 urge sleeve 84 in an axial direction together with cover 86. A slight clockwise rotation of cover 86 with respect to shaft 70 as shown in FIG. 3, causes the ends of pin 88 to move out of extensions 93 due to the friction between the ends of pin 88 and the interior surfaces of groove 90. Since pin 88 resides in groove 90, axial movement of sleeve 84 also causes cylinder 72 to be advanced axially toward distal end 62 and pin 88 to be advanced downwardly along slot 92 after pin 88 has been pushed out of extension 93. Axial movement of both cover 86 and cylinder 72 in a distal direction is limited by the axial extent of slot 92. When such axial force is removed, spring 74 causes pin 88 to return to extension 93, and retracts cylinder 72 and cover 86 toward proximal end 64, and recess 80 returns to its recessed position with respect to walls 69.

Figure 5:
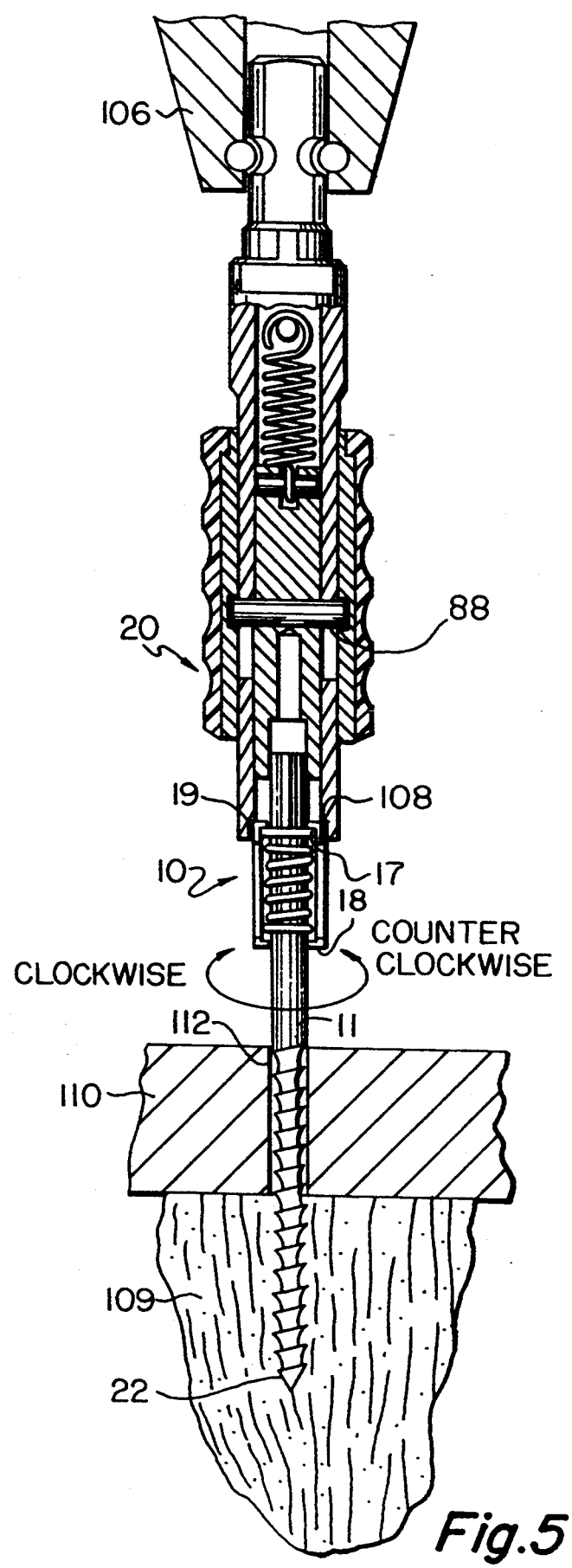
FIG. 5 is a cross-sectional, elevation view showing the insertion of the screw of this invention using the driver of this invention.

The use of screw 10 and driver 20 will now be described with particular reference to FIGS. 5, 6 and 7. Bone 109 in FIGS. 5–7 can be a proximal femur, a proximal tibia or any other bone surface into which it is desired to drive screw 10. Similarly, device 110 shown mounted on bone 109 can be any one of the guides 30 and 40 previously described with respect to FIGS. 1 and 2, or any other device which is to be affixed to bone 109. Device 110 has a previously formed hole 112 through which screw 10 can be readily inserted. If lower surfaces 18 of sleeve 15 are tapered, hole 112 has a chamfered upper portion (not shown) to allow the desired seating of lower surfaces 18 of screw 10 therein.

A known appliance 106 is affixed to coupling 65 of driver 20. Rotation of appliance 106 causes coupling 65, and thus cylinder 72 to rotate in the same direction. In FIG. 5, proximal end 13 of screw 10 is shown extending into walls 69 and recess 80 in its normal operating condition. Upper surfaces of lip 19 rest against shoulders 108 on the interior of walls 69. Shoulders 108 limit axial penetration of proximal end 13 into recess 80. As can be seen, in a normal operating condition, proximal end 13 extends sufficiently far into recess 80 that a tight torque transmitting relationship is produced therebetween such that as appliance 106 is rotated in a clockwise direction, as shown by the arrow in FIG. 5, torque is transferred to proximal end 13 so that a similar clockwise rotation is imparted to screw 10. In FIG. 5, cylinder 72 is in its fully retracted position and pin 88 is seated in extension 93 under the influence of the torque and spring bias of spring 74. Axial force applied by appliance 106 is transferred down shaft 70 to pin 88 which is urged against the proximal surface of extension 93. Pin 88, in turn, transfers this axial force to cylinder 72. Extension 93 prevents any axial movement of cylinder 72 with respect to shaft 70. Cylinder 72 then transfers this axial force to lip 19 which rests on ridge 17 of screw 10. Ridge 17 then transfers this axial force to shaft 11 to drive screw 10 into bone 109.

Figure 6:
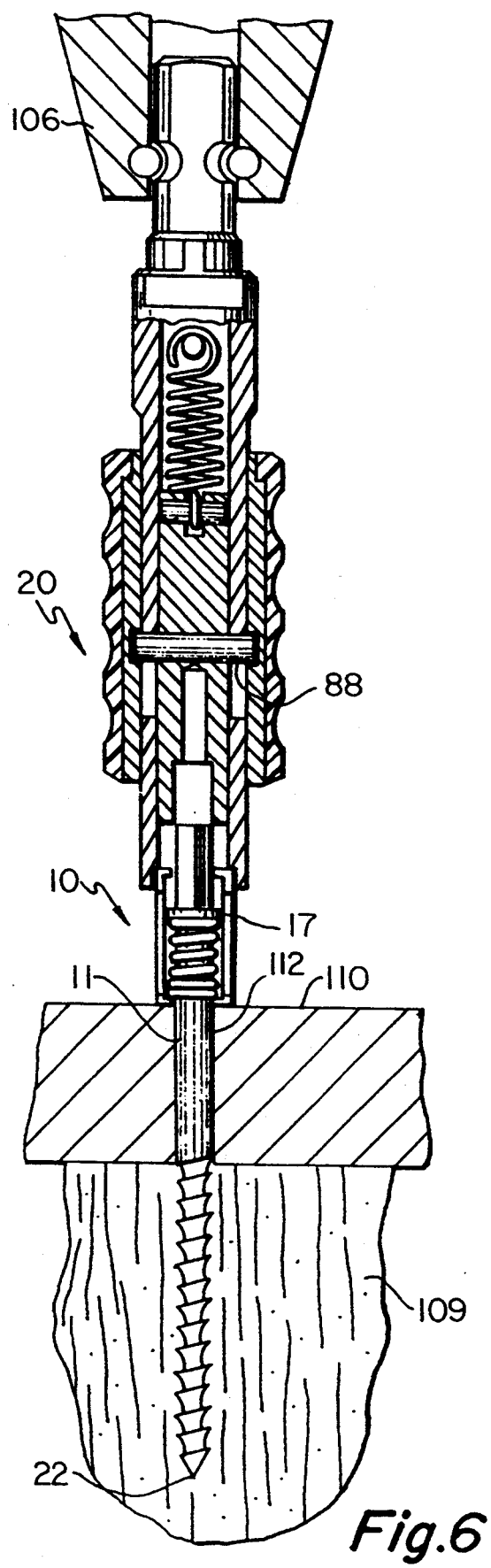
FIG. 6 is cross-sectional, elevation view showing the screw of this invention in its fully installed position.

As shown in FIG. 6, once lower surfaces 18 of screw 10 are fully seated, further axial advance of shaft 11 into bone 108 causes compression of spring 16 between ridge 17 and lower surfaces 18 of sleeve 15, since sleeve 15 cannot penetrate any farther into device 110. This farther axial advance of shaft 11 lifts driver 20 upwardly at shoulders 108, as shown in FIG. 6, causing proximal end 13 to be withdrawn from recess 80 so that surfaces 14 are no longer in torque transmitting relation with surfaces 82 of recess 80. At this point, further clockwise rotation of appliance 106 does not transfer any more rotational torque to proximal end 13. Thus, shaft 11 cannot be driven any farther into bone 109.

Since the penetration of shaft 11 into bone 109 is the same for all such screws and since spring 16 is identical and is compressed an identical amount for all such screws, each such screw applies an identical predetermined load to device 110 to bias device 110 against bone 109. Where two such screws are used, as in FIG. 1, no tilting of guide 30 results. This load has been predetermined to be that needed for the particular application to rigidly secure device 110. Also, the inability to drive shaft 11 farther into bone 108 prevents stripping of the threads by the application of excessive force thereto beyond the point at which surfaces 18 are seated.

Another advantage of this system is that should a screw 10 loosen for any reason during a cutting procedure, spring 16 would continue to apply a load on device 110, thus preventing excessive movement of device 110, despite a loose screw. Prior art screws would permit device 110 to tilt or flop or even move laterally if they loosened. Finally, in the tibial guide of FIG. 2, axial movement of rod 47 is permitted without loosening of screw 10 in slot 44 as rod 47 can be slid along slot 44 against the bias of the spring 16. This movement permits micro-adjustment of the position of platform 50.

Figure 7:
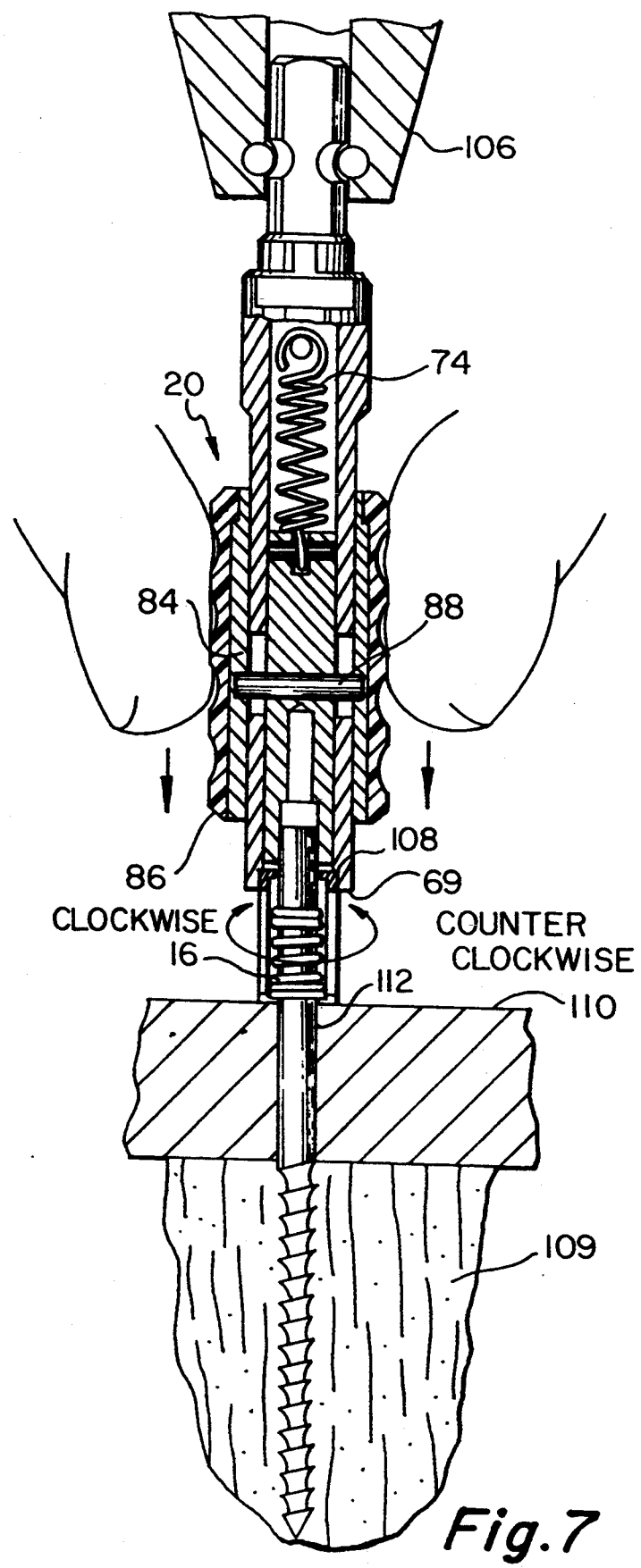
FIG. 7 is a cross-sectional, elevation view showing the extraction of the screw of this invention with the driver of this invention.

FIG. 7 illustrates the removal of screw 10 using the same driver 20. Shoulders 108 again rest on the outer surface of lips 19. The application of a clockwise rotational force to cover 86 causes the ends of pin 88 to drop out of extensions 93. The application of an axial force to cover 86 in a distal direction, as shown in FIG. 7, produces axial motion of cover 86 as well as sleeve 84 toward proximal end 13 of screw 10. This axial movement causes spring 74 to extend and is opposed by spring 74. Distal axial movement of sleeve 84 causes pin 88 to ride down slot 92 toward its distal end, which also causes cylinder 72 to move within shaft 70 in an axial direction toward proximal end 13. Sufficient axial movement of cylinder 72 is permitted such that when pin 88 is seated in the distal end of slot 92, the distal end of cylinder 72 is substantially flush with the distal ends of walls 69. In this extended position, recess 80 of cylinder 72 is now in a position to again re-engage proximal end 13 of screw 10 in a torque transmitting relationship.

The foregoing axial movement can be produced using one hand. Using the other hand, the surgeon can now rotate appliance 106 in a counter-clockwise direction, as shown by the arrow in FIG. 7 either manually, or using a powered appliance. At the same time, the surgeon continues to grip cover 86 with the other hand to maintain the extended axial position of cylinder 72. As appliance 106 rotates shaft 70, cover 86 is prevented from rotation by the hands of the surgeon. Thus, shaft 70 and cylinder 72 rotate with respect to cover 86 and sleeve 84. The rotational torque applied to proximal end 64 is transmitted to shaft 70, and this rotational torque is transferred from shaft 70 to cylinder 72 by pin 88 which bears against the side surfaces of slot 92.

As continued counter-clockwise torque is applied to proximal end 13, screw shaft 11 rides upwardly out of bone 109. Spring 16 urges ridge 17 upwardly toward lips 19 until ridge 17 again abuts lips 19. Once ridge 17 is again seated against the interior surface of lips 19, the situation returns to that shown in FIG. 5. At this point, after release of manual axial force, spring 74 returns cylinder 72, and thus, sleeve 84 and cover 86 upwardly in a proximal direction until the ends of pin 88 are again seated in extensions 93. Proximal end 13 now is engaged by recess 80 without the need of any axial movement of driver 72 by the operator. The surgeon then can continue unscrewing screw 10 in a conventional manner by counter-clockwise rotation produced by appliance 106.

It can be seen that the foregoing screw 10 permits application of a predetermined load on a device at all points thereon to rigidly retain the device in a fixed position and to prevent tilting. Also, this screw prevents stripping of the threads by the application of additional torque once the screw is adequately seated in a preconfigured hole. Moreover, the spring in the screw continues to apply a load to the device, even if it becomes loosened. Finally, fine adjustment of a tibial guide or the like is permitted. The driver 20 associated with screw 10 is capable of inserting the screw and cooperating with the screw to be disengaged from the proximal end of the screw when the proper load has been applied. This same driver can be used for unscrewing of the screw by the unique clutch arrangement provided as described above. Thus, a single tool achieves both insertion and removal, and this tool can be operated by a single person.

Screw 10 and its components can be of any suitable size, depending upon the application. Similarly, driver 20 is typically configured to have the desired size and shape to be able to be used in conjunction with screw 10 and to provide torque and axial force thereto. Sleeve 15 and spring 16 are configured to provide the desired load. Screw 10 and its components, and driver 20 and its components typically are formed of stainless steel or other like hard metals. However, other suitable materials could be used. The foregoing suggested materials are intended in no way to limit the scope of this invention.

In view of the above description, it is likely that modifications and improvements will occur to those skilled in the art which are in the scope of this invention. The above description is intended to exemplary only, the scope of the invention being defined by the following claims and their equivalents.

What is claimed is:

1. A screw adapted to be driven by a driver for removably securing an orthopedic device to a bone surface, said screw comprising:
    a central shaft having a proximal end and a distal end and a central axis extending from said proximal end to said distal end;
    a continuous thread disposed on said central shaft and extending to said distal end of said shaft;
    a coupling disposed on said proximal end of said shaft adapted to be engaged by the driver in torque transmitting relation therewith for rotation of said screw;
    a sleeve disposed about said shaft of said screw, said sleeve being generally coaxial with said shaft and being movable in an axial direction with respect to said shaft, said sleeve having a lower surface facing said distal end of said shaft; and
    a spring for biasing said sleeve away from said proximal end of said shaft;
    wherein advance of said screw in a distal direction into the bone surface after seating of said lower surface of said sleeve causing said sleeve to ride toward said proximal end of said shaft against the bias of said spring to terminate a torque transmitting relationship between the driver and said coupling on said proximal end of said shaft.

2. The screw as recited in claim 1 further comprising a lip disposed on said sleeve and a ridge disposed on said shaft, said lip and said ridge cooperating to limit axial movement of said sleeve toward said distal end of said shaft.

3. The screw as recited in claim 1 wherein said spring is compressed as said screw advances into the bone after seating of said lower surface of said sleeve.

4. The screw as recited in claim 3 wherein said spring provides a predetermined load when it is sufficiently compressed that there is no longer a torque transmitting relationship between the driver and said coupling.

5. Apparatus for removably securing an orthopedic device to a bone surface, said apparatus comprising:
    a screw having a proximal end, a distal end, an axis extending from said proximal end to said distal end, and a continuous screw thread extending about said screw to said distal end;
    a driver having a proximal end and a distal end, said distal end of said driver having a recess configured to receive said proximal end of said screw for transmission of torque from said driver to said screw; and
    a sleeve disposed about said screw and being biased toward said distal end by a spring, said sleeve having lower surfaces facing said distal end of said screw, said sleeve moving axially along said screw toward said proximal end against the bias of said spring when said lower surfaces of said sleeve are seated to remove said distal end of said driver from said proximal end of said screw so that said proximal end of said screw is not received in said recess to prevent the further transmission of torque from said driver to said proximal end of said screw.

6. The apparatus as recited in claim 5 further comprising:
    a shaft on said driver having a central axis;
    a cylinder disposed within said shaft and being axially movable with respect to said shaft, said cylinder having said recess formed on a distal end thereof; and
    a manually actuable mechanism for moving said cylinder and said recess axially with respect to said shaft toward said proximal end of said screw to permit receipt of said proximal end of said screw in said recess in a torque transmitting relationship for removal of said screw.

7. The apparatus as recited in claim 6 wherein said manually actuable mechanism comprises:
    a sleeve on said driver disposed about said shaft, said driver sleeve being rotatable with respect to said shaft about the central axis of said shaft;
    a mechanism coupling said cylinder to said sleeve; and
    a spring biasing said cylinder axially away from said proximal end of said screw.

8. The apparatus as recited in claim 7 wherein said mechanism comprises:
    a channel formed on an inner surface of said sleeve and extending around an entire circumference of the inner surface of said sleeve;
    a pin coupled to said cylinder and extending into said channel; and a slot disposed in said shaft through which said pin extends, said slot extending an axial direction with respect to said central axis of said shaft.

9. The apparatus as recited in claim 8 wherein said shaft includes an extension of said slot extending at an angle with respect to the direction of elongation of said slot, whereby as rotational torque is applied to said proximal end of said driver to drive said screw into the bone, said pin is urged into said extension and against end surfaces thereof to prevent unwanted axial movement of said cylinder with respect to said shaft.

10. The apparatus as recited in claim 6 further comprising surfaces on a distal end of said shaft extending distally beyond said recess in said cylinder when said cylinder is in a normally retracted position, said distal surfaces on said shaft having a shoulder formed on interior portions thereof for engagement of said sleeve of said screw.

11. Apparatus for rotating a screw having a shaft with a central axis, a distal end having a continuous thread extending thereto, a proximal end adapted to be coupled to said apparatus in a torque transmitting relationship, a sleeve disposed around the screw shaft between the proximal and distal ends of the screw and a spring biasing the sleeve away from the proximal end of the screw, said apparatus comprising:

a shaft having a proximal end, a distal end and a central axis, said proximal end of said shaft being adapted to be coupled to an appliance for providing rotational torque to said shaft about said central axis of said shaft, said distal end of said shaft having a generally cylindrical, centrally disposed cavity formed therein;

a cylinder disposed in said cavity of said shaft, said cylinder being configured to receive in a torque transmitting relationship the proximal end of the screw;

a spring biasing said cylinder away from said distal end of said shaft;

a sleeve disposed about said shaft, said sleeve being slidable in an axial direction with respect to said shaft and being rotatable about said central axis of said shaft; and a mechanism coupling said cylinder to said sleeve whereby axial force applied to said sleeve toward said distal end of said shaft causes said cylinder to move axially with respect to said shaft toward said distal end of said shaft.

12. The apparatus as recited in claim 11 further comprising a shoulder disposed on interior surfaces of said cavity of said shaft to limit penetration of the screw sleeve into said cavity.

13. The apparatus as recited in claim 11 wherein said mechanism comprises a pin coupled to said cylinder and extending through a slot in said shaft and into a channel in said sleeve.

14. The apparatus as recited in claim 11 wherein as the sleeve on the screw seats, continued application of torque to the screw causes the screw shaft to advance axially with respect to the screw sleeve so that the proximal end of the screw retracts into the screw sleeve until the proximal end of the screw is withdrawn from engagement with said cylinder.

15. The apparatus as recited in claim 11 further comprising a clutch mechanism for preventing unwanted axial movement of said cylinder with respect to said shaft when torque is being applied to said apparatus in one direction and for permitting axial movement of said cylinder with respect to said shaft when torque is being applied to said apparatus in a direction opposite of said one direction.

16. In combination, a cutting guide and screw assembly for resecting bone, the cutting guide including at least a first opening for receiving a cutting instrument and at least a second opening for receiving the screw assembly, the screw assembly comprising a shaft with a threaded end for insertion into a bone and a spring, said spring being engageable with the shaft and the cutting guide for applying a load to the cutting guide to bias the cutting guide against the bone.

17. The combination as recited in claim 16, further comprising:

a sleeve disposed about said shaft, said sleeve having lower surfaces for bearing on the cutting guide and being movable with respect to said shaft in an axial direction generally parallel to a direction of elongation of said shaft; and a ridge disposed on said shaft, said spring being captured between said lower surfaces of said sleeve and said ridge, whereby axial advance of said shaft with respect to said sleeve toward the cutting guide compresses said spring.

18. The combination as recited in claim 17, wherein said sleeve is formed of a metal.

19. The combination as recited in claim 17, wherein axial movement of said ridge away from the cutting guide is limited by a lip disposed on said sleeve spaced from said lower surfaces of said sleeve in said axial direction.

20. The combination as recited in claim 16, wherein compression of said spring applies a load to the cutting guide.

* * * * *